Figure 1:
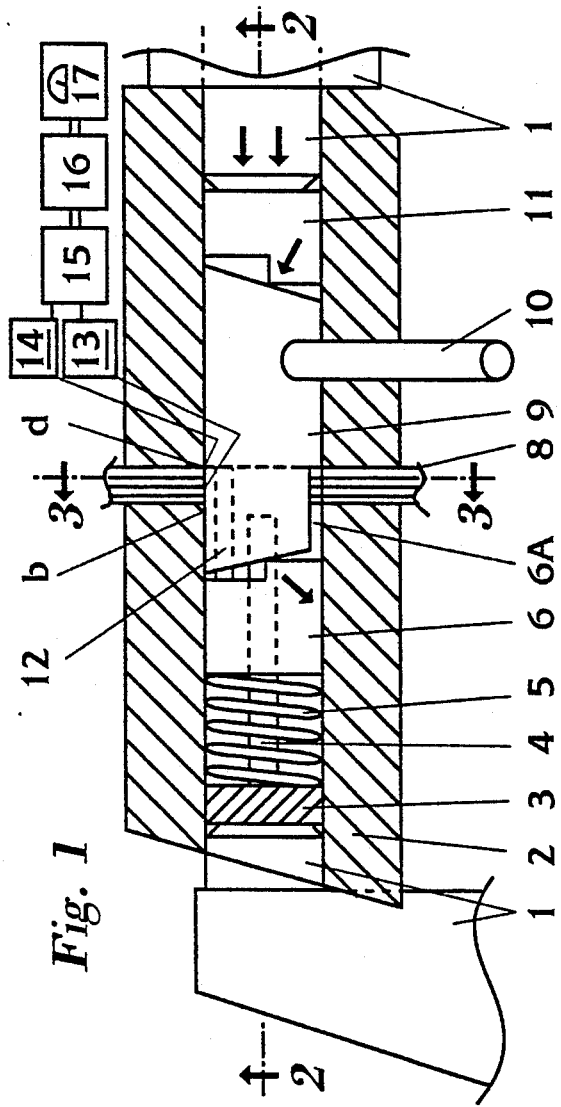

United States Patent [19]

Nissimov

[11] Patent Number: 5,327,656
[45] Date of Patent: Jul. 12, 1994

[54] DEVICE FOR OVERALL DIAMETER MEASUREMENT OF A GROUP OF HAIRS OR FIBERS (ODMOGH)

[76] Inventor: Joseph Nissimov, P.O. Box 1487, Jerusalem 91014, Israel

[21] Appl. No.: 944,222

[22] Filed: Sep. 14, 1992

[30] Foreign Application Priority Data

Mar. 8, 1992 [IL] Israel ........................ 101174

[51] Int. Cl.⁵ .............................................. A61B 5/107
[52] U.S. Cl. ........................................ 33/512; 128/774
[58] Field of Search ............... 33/512, 511, 783, 813, 33/555.1, 555.2; 128/774

[56] References Cited

U.S. PATENT DOCUMENTS

| | | | |
|---|---|---|---|
| 869,697 | 10/1907 | Eilhauer et al. | 33/813 |
| 1,962,357 | 6/1934 | Nessler | 33/512 |
| 1,962,518 | 6/1934 | Nessler | 33/512 |
| 5,107,853 | 4/1992 | Plyter | 33/512 |

*Primary Examiner*—William A. Cuchlinski, Jr.
*Assistant Examiner*—C. W. Fulton

[57] ABSTRACT

A device which measures the overall diameter of groups of hairs or fibers and reduces the work required to obtain their statistical parameters. In the preferred embodiment an outer hollow cylinder is mounted between the measuring surfaces of a micrometer. An inner edge of a trough made in the cylinder articulates with an edge of a half cylindrical portion of a piston moving within it by means of a handle; the two parts thereby making a window with diametrically opposed halves. A spring presses the piston edge to the trough edge by sliding the piston on slopes against two parts with short steps and a block disengages one end of the piston to let hair in when open. An elongated step with a railing is placed under the piston half cylinder thus making the window into a face of a hollow triangular prism. The railing rises higher than the edge of the trough so that when the piston and trough edges nearly meet the elongated bottom step must turn and bend the hairs. Closing the window in one dimension therefore lays the hair single file and on their major ellipsoidal axis. In the second dimension the hairs slide with minimal friction due to their edge contacts within the device. When the fibers begin to compress one another they tilt characteristically and their total thickness can be read by the micrometer. A hair stop placed under the functional corner of the trough maintains the hair perpendicularly oriented in the window.

6 Claims, 1 Drawing Sheet

DEVICE FOR OVERALL DIAMETER MEASUREMENT OF A GROUP OF HAIRS OR FIBERS (ODMOGH)

Introduction

The device for the Overall Diameter Measurement of a Group of Hairs or Fibers (ODMOGH) was developed mainly for measurements of hair fibers' diameters and for this reason the introduction relates to the operation of the device to that end. There is no doubt however, that other fibers may be measured by the device and they are therefore also included as being within the scope of its application. At this time I am not aware of any specific applications for the group measurement of fibers' diameters in addition to that of hair.

The hair fiber diameter has an important place in the fields of hair esthetics, molecular structure, and medicine. On the one hand it is one of the most important factors for hair style stabilization and the conferring of volume to the hair, and on the other hand it is easily influenced and accessible to measurement during certain physiological states or through artificial disturbances. In order that the hair fiber diameter may be used in these fields it should be measured comparatively and with maximal accuracy, but until now a general and simple method to do so has apparently not been found.

Methods for the hair fiber diameter determination may be classified as group methods or single fiber methods. Group methods have an advantage from a statistical point of view due to the large sample size which may be used. However, they are indirect methods for diameter measurements in that they usually compare before and after weights or volumes, and they are therefore usually inaccurate or are prone to systematic errors. An additional disadvantage of group methods is that regardless of the size of the group measured, the hair need to be counted and the measurement performed several times in order to evaluate the important statistical parameter of the biological variability of the hair. Since large groups of hair are difficult to count and since the differences between average groups of hairs' diameters become smaller as the group size increases the hair variability measurement becomes more difficult with larger groups of hair. The variability of the hair diameter may change in certain conditions such as in balding, and therefore, it may be desirable to know it in such cases as without it's knowledge diagnosis or the effect of treatments may be lacking.

Single fiber methods for diameter measurements measure the diameter directly and therefore the uncertainties in interpretations of the results of indirect measurements are avoided. Microscopic methods, which might seem to be methods of choice from among these, are unfortunately not very suitable for the diameter determination of the hair. The unsectioned hair fiber is usually too thick to focus onto a single plane with an optical microscope. Electron microscopy on the other hand is damaging to the hair either in preparation or the examination.

The main problem which limits the routine use of single fiber diameter measurements is the large amount of work that is required for the determination. The work for preparation of a single hair fiber is compounded by the requirement to repeat the measurement of the same fiber before and after treatment, as well as on several hair fibers. Although by measuring the same hair at the same place before and after treatment the biological variability of the diameters may be eliminated as a complicating factor it is still possible that the response of different hairs to the same treatment may be different. Therefore, the measurement of a single fiber would not be sufficient and it would require several measurements in order to obtain reliable results.

The device herein described and for which the patent is applied combines the positive aspects of mass and single fiber measurements. The device measures the overall diameter of a limited group of fibers which are placed on a single plane in a row and are thus easily countable. The statistical variability of the groups measured is thereby also easily determinable, and the efficiency of the measurement in terms of savings of time and work is similar to that of mass measurements. The device described is usable in practically any situation and is a general method for the hair fiber determination. These advantages appear to make it the best available method today for the hair diameter determination.

DESCRIPTION OF THE DEVICE AND ITS OPERATION

FIG. 1. Schematic diagram of the device for the Overall Diameter Measurement of Groups of Hair or other fibers (ODMOGH)—side view.

Figure 2:
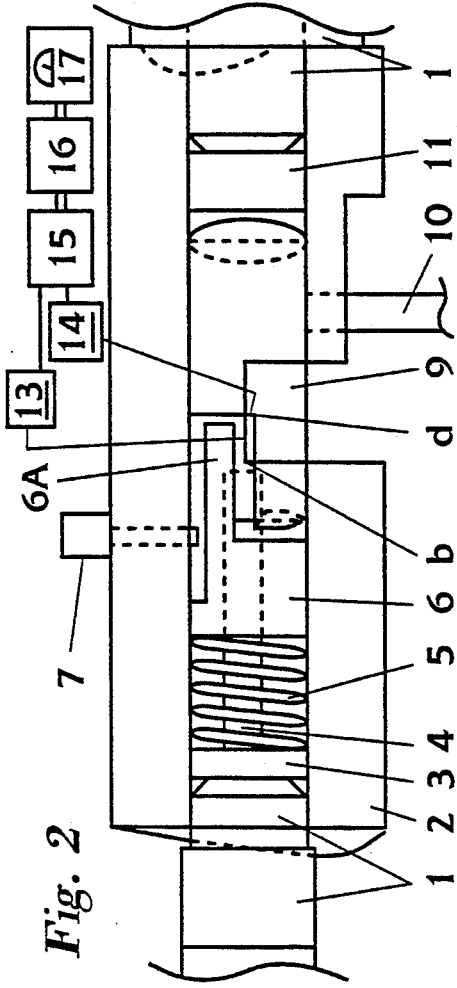

FIG. 2. ODMOGH—view from above.

Figure 3:
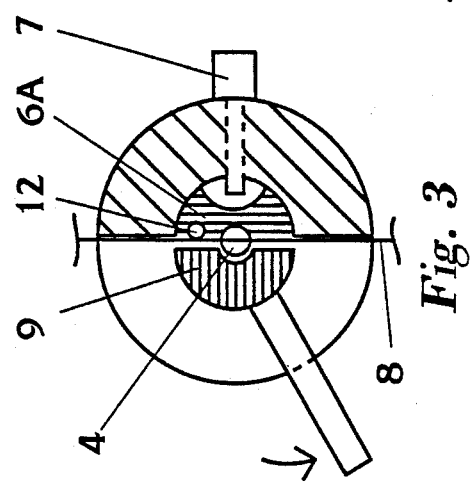

FIG. 3. ODMOGH—cross section with hair in free position.

Figure 4:
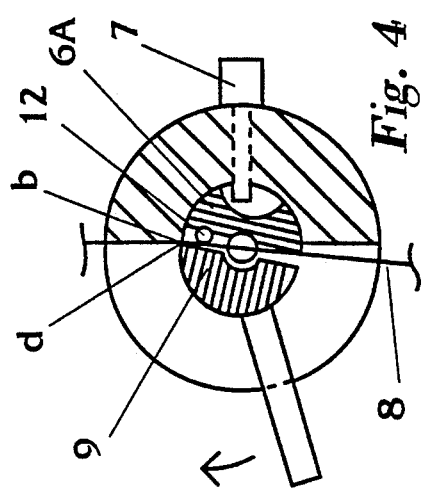

FIG. 4. ODMOGH—cross section with hair bent during measurement.

FIGS. 1-4 show schematic diagrams of a working model of the ODMOGH. Routinely between 10-25 hairs were measured simultaneously by the working model built but there is no impediment for measuring a single hair fiber with the device or a greater number of hairs than 25. The functional part of the device incorporates a window which opens and closes in two dimensions while in the third dimension its parts remain essentially on a single geometric plane. The window is constructed from two reciprocal halves having the form of a half rectangle each, whose diametrically opposing corners can be brought close to one another in two dimensions until there is no space between them. This feature of the window is guaranteed by the two corners being in fact able to get one past the other in the two dimensions. One half of the window is stationary (b) and it is formed by filing a trough in the outer hollow cylinder of the instrument (2) to approximately half its thickness, and to a width of about 0.5 cm. A piston (9), which moves within the outer cylinder of the instrument is also filed to a length of approximately 0.5 cm and to about half its thickness thus forming an "elongated step" and the moving part of the window (d). By use of a handle (10) the piston can be turned inside the outer cylinder of the instrument and thereby the vertical distance between one of its filed edges and the inner filed edge of the outer cylinder of the instrument may be brought to zero (and to less than zero as well). By this operation all the hairs which are placed between the two parts can be laid on a single plane. Hairs which are found one above the other slide and come to rest side by side. Since hair is generally elliptic they also generally lay on their major axis. The outer cylinder of the device (2) is mounted on a commercial micrometer (1) by slopes at its ends which allow its insertion between the anvil and piston of the micrometer at an angle. Rotating the outer cylinder after it is fitted around these parts then presses it tight against the micrometer body (FIGS. 1 and 2).

When the micrometer piston is made to approach the micrometer anvil the ODMOGH piston (9) is pushed ahead of it and the mobile corner of the window (d) approaches its stationary corner (b). In this way it is possible to bring all the hairs from a state with spaces among them to a state of an absence of spaces (FIG. 1). When there are no hairs between the mobile corner of the window and the stationary corner the two may be brought closer until there is an absolute absence of space between them and in this position the instrument may be calibrated. The piston may also be moved backwards until a passage is opened between it and the window half which is cut in the outer cylinder of the device. In this position the hair is inserted into the window for diameter measurements and taken out after the measurement. When the passageway between the ODMOGH piston and the outer cylinder is closed (FIG. 2) the hairs are closed in within the window.

The two halves of the window are brought close to each other as much as possible on the plane at which they move alongside each other (in the third dimension). Otherwise a moment of force can be created between them which can cause the hairs between the two parts to bend in the two dimensions in which the window closes and thereby bring about inconsistent results in measurements. Only when the distance between the two parts is zero can the possibility of the hairs' bending for this reason be eliminated. This was achieved by adding two parts having short steps at the two ends of the piston which pushed it during the measurement towards the internal wall of the ODMOGH cylinder (6 and 11). The right direction for pushing the piston was given to it by filing it at its ends with slopes at an angle of 90° to the edge and the filed plane surface of the moving half of the window. Since one end of the piston was already filed to about half its diameter the slope at this end was made in the half of the piston remaining, or in a quarter of a circle of the surface of the piston end. The matching step for it (in part 6) was made as a trough in the shape of a quarter circle into which the slope at the end of the piston could loosely fit. The slope at the other end of the piston was made in half of the piston cylinder as the piston was not previously filed at that end. Its matching step was along a line of about half the diameter of part 11 which supported the piston slope at that end.

The slopes at the ends of the piston come in contact with the steps in parts 6 and 11 which, when lateral pressure is put on them, cause the piston to slide on the steps until it is stopped by the internal wall of the ODMOGH cylinder, or in other words, when the space between them is zero (FIG. 1). When the piston turns parts 6 and 11 turn with it because of the line contact between them and the piston and therefore the direction of the force on it is always at an angle of 90° to the horizontal edge of the moving window. When the hairs in the window are brought to the thickness of a single file (approximately 70 $\mu$m) the two filed surfaces of the half windows are brought close to being on a single plane and are pressed with great precision towards each other. (An even greater precision in pressing the two edges of the half windows towards each other could be obtained if the angles between the edge and plane surface of the filed piston and the slopes at its ends were made slightly greater than 90°, to compensate for the thickness of the hair file.) This way of pressing the piston to the internal wall of the ODMOGH cylinder also eliminates a result of lowering in accuracy of the instrument with time due to chafing and wearing: Since the piston is always pressed to the window, the tolerance between them always strives for zero.

The moving force for pressing the ODMOGH piston to the inner wall of the instrument cylinder is derived from a spring to the left of the piston (5). The spring also returns the piston backwards when the micrometer is opened and makes possible the opening of a passageway between the piston and the trough in the outer cylinder of the ODMOGH, through which the hairs are inserted for measurement and taken out. Actually, the opening of the passageway for the hairs is prevented when the spring pushes part 6 onto part 9 because the two are in contact, and it is necessary to free the contact between them when the piston end reaches to a line under the cut of the window (below point b) in the cylinder. This result was attained by placing a block (7) for part 6 at the bottom of the outer cylinder. The bottom of part 6a, (which is an extension of part 6 in the working model) was filed in order to allow the part to freely turn and move over the block (FIGS. 2, 3, and 4). But when the lateral movement reached a certain point it could no longer advance (FIG. 2), and part 9 was released from contact with part 6 and the pressure from the spring that pushed it.

With the device as described above consistent measurements of the diameter of a group of hairs could be obtained. However, the measurement is technically inefficient and requires many operations of back and forth movements of the piston in order to orient the hair perpendicularly to the window surface. Without this orientation of the hair they would line themselves diagonally in the window due to friction with its parts as it closes and would present sections along variable parallel angles to be measured. In order to solve this problem a hair stop (4) was put in, which prevented the hair from entering diagonally between the window parts (FIGS. 1 and 3).

The hair stop base (3) is pressed to the anvil of the micrometer by means of the spring which moves the ODMOGH piston and therefore the hair stop does not move during the measurement. The free end of the hair stop is found exactly under the stationary corner of the window (b) so that when the hairs are pushed beyond an imaginary line to the left of point b and the free end of the hair stop, they are blocked by the hair stop and are forced to straighten and become oriented parallel to this line.

In order to allow for part 6 which moves around the hair stop while the hair stop does not move to continue in this motion a hole was made at it's center through which the free end of the hair stop was inserted. In order that the hairs would not enter above the hair stop or below it part 6 was built also with an "elongated step" (6a) which was complementary to and fitted under the filed half of the ODMOGH piston. The gap between the upper step of the ODMOGH piston and the lower elongated step (6a) is smaller than the diameter of the hair stop cylinder. In order to allow the parts to continue to move unhindered alongside it, channels were made in them in the shape of half circles. The channels then envelope the hair stop together as a circle with a wider diameter than the hair stop cylinder and so the parts may move alongside it (FIGS. 3 and 4). The channels also cause the hairs, when they are between parts 6a and 9, to remain in the gap between them without becoming wedged between the parts. The only way that the hairs could enter into the space between the hair stop and the steps of parts 6a or 9 is to bend unnaturally first upwards and then downwards, or vice versa.

The lower long step (6a) which was given to part 6 also allowed to detract from an additional problem in the diameter measurements caused by loose fitting of some of the hairs in the window. Since the hairs are not all of uniform diameter there are situations in which a smaller hair, or a group of hairs, are found between two thicker hairs. Because on these hairs only lateral pressure is put during the measurement they are free in principle to turn between the other hairs in the device and since hair is usually elliptical, this may cause inconsistent results in the diameter measurements.

A sufficient solution to this problem was made possible by a self-pressing of the hairs from down upwards, to the roof of the moving half of the window in the ODMOGH piston. Along the lower elongated step (6a) near the wall of the outer cylinder, a thin cylinder was placed thus making a railing (12). The height of the lower step with this railing is such that it is considerably greater than the stationary half of the window, but of course less than the moving half of the window which is complementary to and above it (FIGS. 2 and 3). When the moving half of the window is brought to nearly the same level as the stationary half, the lower elongated step must turn, not only because of the contact between the slope in the piston and the short step in part 6, but also because contact is created between the filed surface of part 9 and the railing of part 6a. Since an angle is thereby created between the plane surfaces of parts 6a and 9 and the surface near the edge of the stationary half of the window (FIG. 4), any hairs resting on the railing are forced to bend. As an opposing reaction to this bending the hairs are pressed to the edge of the ODMOGH piston also from down upwards. This pressing is derived from an elastic resistance of the individual hair's bending and it is not dependent on it's diameter so that it is given to all the hairs in similar measure. For this reason also, the hairs tend to lay themselves on their major axis. A standard error of the mean with the working model of the instrument, of about 0.4% when measuring 10 groups of hairs twice each, approached the limit of resolution of optical microscopy and proved that turning of the hairs within the device indeed does not lead to a large error. It is conceivable that an even smaller error might be obtained with more precise machine building of the device.

The leaning of the hairs on the cylinder of part 12 created a point contact between it and the hairs and it also prevented contact between the hairs and part 6a in all but one point. Thus, friction was minimized between part 6a and the hairs and the minimal friction between the hairs and parts 6a, 12, and the essentially depthless edges of the measuring window allowed the hair to slide with relative ease in the window. There is no reason why the long lower step (6a) may not be a separate part from part 6 and it is possible that separating the two parts will improve the functioning of the device.

The geometry which is created between the edge of the stationary half of the measuring window, the edge of the moving half of the measuring window, and the railing (12) of the lower elongated step can be described as a hollow triangular prism, whose upper edge is formed by the edge of the moving half of the window. The hairs are pinched between the lower edges of the prism and the upper edge when it descends on them by turning the piston handle (FIGS. 3 and 4). The hairs are also pinched between the ends of the prism from right to left when from the left they are stopped by the stationary corner of the window (b) and the free end of the hair stop (4) and form the right they are pressed by the moving corner of the window (d), (FIGS. 1 and 2).

In practice the hair diameter measurements were carried out in the following manner: Before each series of diameter measurements the device calibration was checked and reset if necessary. The hairs were put into the ODMOGH attached with a sticky tape at their ends and the tape stopped the hairs form entering the device beyond the contact point between it and the outer cylinder of the ODMOGH. Since the wall of the outer cylinder was about 3 mm thick the hair groups were measured at that distance form their point of attachment with the tape. The end point of the measurement was obtained by a process of narrowing between too much space between the hairs and too little space, or compression, of the hairs. When the separations between the hairs reached zero and they were brought even closer together a synchronous movement was given to all of them which appeared as a concerted tilting of all the hairs in the direction of the ODMOGH piston. The point at which this movement was initiated was easy to distinguish, especially when it was identified in a dynamic manner by repetition several times, and it was taken to be the overall diameter measurement of the hairs in the device.

The ODMOGH was tightened on the anvil and the piston of the micrometer so that the edge of the window in the outer cylinder of the device was approximately at an angle of 45° from the vertical and the ODMOGH horizontal axis. For reasons of convenience the measurements were usually made while looking through a stereoscopic dissecting microscope with a magnification of 10-40 times. However, use of the microscope is not essential due to the characteristic tilting motion of the hairs when they touch one another and therefore the measurement as it was performed is considered to be a mechanical measurement in principle, which can be carried out in an optical manner.

By counting the number of the hairs in the device when they are laid side by side in a row and dividing their total diameters by their number the average diameter of the hairs in the device can be obtained. By repeating this process on several groups of hair the instrument can be therefore conveniently used for the estimation of the biological variability of the hair, in contrast to other group methods. Usually there is no need to know the average diameter of the hairs, when they are treated for example with substances, because even in that case the instrument may be used. The difference in diameters in this case is simply calculated in percent by comparing the overall diameter of the hairs after the treatment to that before the treatment.

The device was built from Plexiglass with an inner piston diameter of 0.6 cm but it can also be built from other materials and/or with different inner piston and outer cylinder diameters. The configuration of the working model of the device as described above is not critical and it is possible to build the instrument where instead of two cylinders that make a window between them the hairs are enclosed between two other surfaces. For example, the two halves of the window may be delimited by interdigitating comb like halves, with corners at their diametrically opposing ends, which can move alongside and upwards and downwards in relation to each other. The geometry which will enclose the hairs in this variation of the instrument will be that of a single or multiple rectangular prisms, depending on the number of teeth of the interdigitating combs. The problem of diagonal orientation of the hair within the window therefore will not arise with it since two rectangular windows in each of the rectangular prism(s), formed by one tooth of the interdigitating combs on one side and at least two teeth on the other, will make hair stops for one another. In this variation therefore, it would not be necessary to include the hair stop (4) as in the piston ODMOGH. It should be pointed out, however, that the piston ODMOGH would result in the least resistance to the hair sliding of all the possible "hollow prism/s" hair enclosing devices since in this device the minimum of edges would come in contact with the hair.

It can be presumed that it would also be possible to build the instrument in other additional configurations or variations. For example, it is possible to create a contact between the two halves of the window by a magnetic attraction between them rather than through parts 6 and 11. It is also possible that by precision fitting of the ODMOGH piston to the inner diameter of the outer cylinder parts 6 and 11 could be dispensed with while the device would still yield highly accurate results.

Because the hairs are laid on their major axis during the measurement it is possible to use the instrument for the measurement of their minor axis as well. Pressure sensors may be added to the surfaces which come in contact with the hair (13,14), so that when the hair begin to be compressed the sensors will indicate so. These sensors may operate in the two dimensions along which the measuring window of the ODMOGH closes and not only in one. Also, the thickness of the hairs in the two dimensions may be read not in a mechanical manner as with a micrometer but by means of a photoelectric cell, or by other means (FIG. 2).

By measuring the amount of light that passes through the window when the hair fill it exactly and comparing this quantity to the amount of light which would pass through the window at the same opening without the hair it would be possible (with appropriate corrections) to find not only the average thickness of the hair in their major axis, but also in their minor axis. These two parameters together would give the average cross sectional area of the hair which is in reality the important factor for assessing its mechanical properties. Other additions could probably also be found in order to count the number of the hairs in the window automatically, etc. All the above variations and additions are also included in the scope of the device as being facilitated by and incorporating a two dimensional window which closes along a single plane from an indefinite size to zero in both dimensions. They are indicated in the drawings (FIG. 2) in a general way by extending from sensors (13,14), in or around the window, input lines to a measuring device of one of the types specified (15). From this generalized measuring device a transducer (16) converts the signal to a quantitatively interpretable signal which is then displayed on a display mechanism (17).

I claim:

1. A device for the measurement of the overall diameters' thickness of a group of adjoining fibers arrayed in a single file, comprising:

(a) a hollow outer cylinder formed with a cutaway trough, said trough extending substantially through and communicating with the interior of said cylinder, said trough extending part way along the radial axis of said cylinder;

(b) a piston located within said cylinder, said piston being slidably independently translatable and rotatable with respect to said cylinder, said piston featuring a cylindrical portion and a substantially half-cylindrical portion, said half-cylindrical portion having a thickness which is significantly less than the depth of the cutaway trough in said hollow cylinder, the boundary between said cylindrical portion and said half-cylindrical portion forming a step;

(c) means for translating said piston;

(d) means for rotating said piston; and (e) means for measuring the longitudinal position of said piston with respect to said cylinder;

the device characterized in that after a group of fibers is placed in said cutaway trough said piston is rotated so that a functional edge of the half-cylindrical portion of said piston presses the fibers to an opposing functional edge of the bottom of the trough to cause them to be arrayed in a single file, and said piston is translated so that a functional edge of said step of said piston causes the fibers to adjoin one another by pressing them to an opposing functional edge in the wall of the trough.

2. A device as in claim 1, further comprising means for urging said functional edges of the piston half-cylinder toward said functional edges in the trough so as to cause said edges of said parts to slide alongside each other on an essentially single geometric plane.

3. A device as in claim 2, further comprising means for orienting the single file of fibers on their major ellipsoidal axis including:

(a) a substantially half-cylindrical part complementary to, and situated under, the half-cylindrical portion of the piston of said device, said complementary half-cylindrical part having a functional edge near the functional edge of the piston half-cylinder, said edge rising significantly higher inside the hollow cylinder than the bottom of the trough of said cylinder;

(b) said complementary half-cylindrical part being additionally suitably sculpted so that it is translatable and rotatable substantially freely within the hollow cylinder of the device; and the operation of the half-cylindrical portion of the device piston, the bottom of the trough, and said complementary half-cylindrical part in conjunction being characterized in that when the three functional longitudinal edges of the parts are nearly at the same level the complementary half-cylinder must turn causing fibers lying on its surface to be at an angle relative to the surface of the bottom of said trough and to bend.

4. A device as in claim 3, further comprising means for aligning the fibers so as to cause said fibers to orient themselves substantially perpendicularly to the radial axis of said cylinder when said piston is translated to cause the fibers to adjoin one another.

5. A device as in claim 4, further comprising means for detecting the point at which the fibers have been adjoined and have been properly arrayed in a single file.

6. A device as in claim 5, further comprising means for measuring the height of the arrayed single file of fibers as well as their overall width.

* * * * *